United States Patent [19]

LaHaye

[11] 4,269,307
[45] May 26, 1981

[54] INTRAOCULAR LENS STORAGE ASSEMBLY

[75] Inventor: Peter G. LaHaye, Diamond Bar, Calif.

[73] Assignee: Iolab Corporation, San Dimas, Calif.

[21] Appl. No.: 65,366

[22] Filed: Aug. 9, 1979

[51] Int. Cl.³ .................... B65D 81/18; B65D 25/54; A61F 1/16; A61F 1/18
[52] U.S. Cl. ................... 206/5.1; 206/45.34; 220/345; 356/246
[58] Field of Search .................. 206/5.1, 210, 45.34; 220/345; 356/246

[56] References Cited

U.S. PATENT DOCUMENTS

| | | | |
|---|---|---|---|
| 3,268,068 | 8/1966 | Le Grand | 206/5.1 |
| 3,406,821 | 10/1968 | Weissberg | 220/345 |
| 4,113,088 | 9/1978 | Binkhorst | 206/210 |
| 4,173,281 | 11/1979 | Trought | 206/5.1 |

Primary Examiner—William T. Dixson, Jr.

[57] ABSTRACT

An intraocular lens storage container assembly that permits a visual inspection of the diopter power and size of the lens without removal from the container is provided. A transparent outer housing permits the transmission of light without any substantial distortion. A support member is configured to fit within the transparent outer housing and has at least one transmitting area that also permits the transmission of light without substantial distortion. A retention configuration is provided on the support member for securing the intraocular lens on the support member and a lid member is capable of locking the intraocular lens into a set position.

4 Claims, 6 Drawing Figures

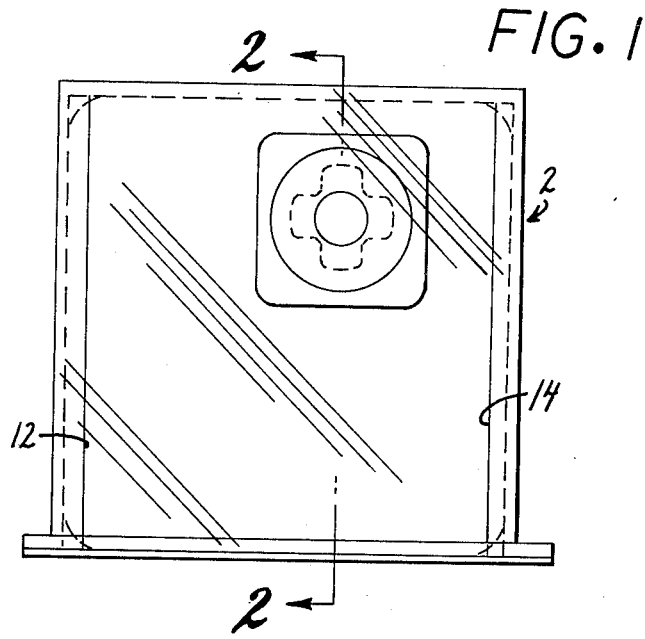
FIG. 1
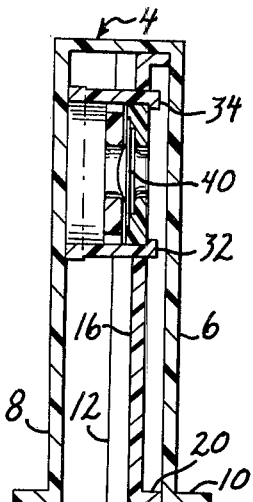
FIG. 2
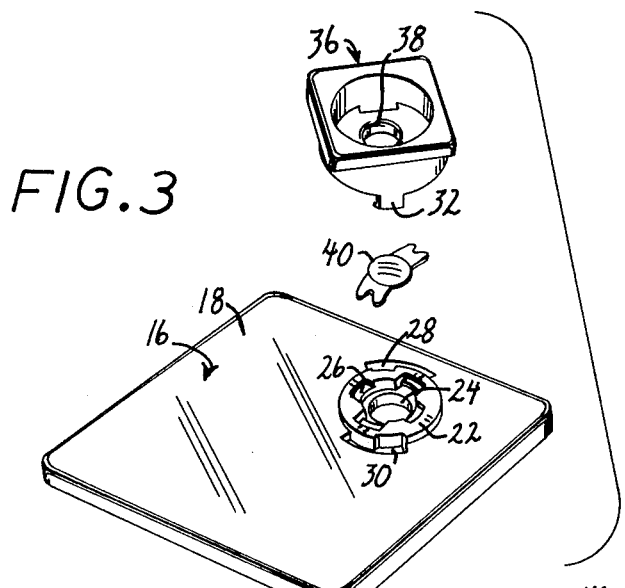
FIG. 3
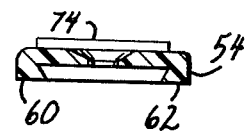
FIG. 5
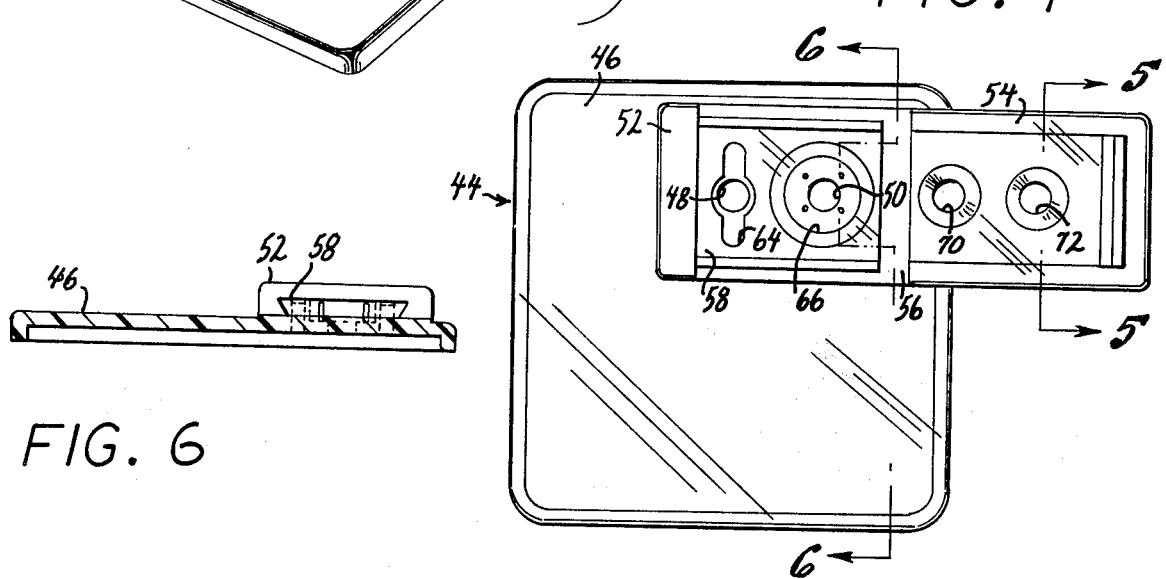
FIG. 6
FIG. 4

INTRAOCULAR LENS STORAGE ASSEMBLY

BACKGROUND OF THE INVENTION

1. Field of the Invention

The present invention is directed to a storage container assembly for sterile objects that should be visually inspected while maintaining a sterile environment and more particularly to a storage container assembly for intraocular lenses that permits a visual inspection of the lens portion while preserving the sterility of the intraocular lens.

2. Description of the Prior Art

Intraocular lenses are used to restore sight to a person who has had his natural lens removed, for example, after a cataract operation. The intraocular lenses are actually inserted within the anterior or posterior chamber of the eye. Since these lenses effect the vision of the patient it is important that the proper diopter power be correctly diagnosed and the appropriate lens having that diopter power be inserted in the patient's eye. Additionally, the size of the lens is very important.

Because these intraocular lenses are implanted into the eye, it is important that they be sterile to prevent any infection. Frequently, a doctor will have a plurality of intraocular lenses available at the time of the implanting operation and will inspect the diopter power prior to implanting. Various types of sealed containers, some containing a fluid, have been utilized to store intraocular lenses.

Once the intraocular lens is removed from its container, the sterile environment is lost and if the package containing the wrong diopter power lens has been opened, it is necessary to return that lens to the manufacturer for resterilization. Since the lenses are manufactured to precise specifications, there is an additional risk of damage to the lens during the interim handling and the mailing of the lens back to the manufacturer.

Accordingly, the prior art has suffered from problems of extra expense and damaged lenses as a necessary incidence of the business.

SUMMARY OF THE INVENTION

The present invention is directed to an intraocular lens storage container assembly that permits a visual inspection of the lens portion of the intraocular lens without removal from the container. A transparent outer housing having a pair of parallel walls capable of transmitting light without any substantial distortion is provided. A support member is configured to fit within the transparent outer housing and provides one or more apertures for storing one or more intraocular lenses. A recessed portion of the support member is provided adjacent the aperture and is of such a dimension and configuration to receive the haptic portions of an intraocular lens. The optic lens portion being thereby positioned over the aperture. Alternatively, a plurality of posts could be positioned about the aperture for receiving the loops that are commonly used on the haptic portions of posterior chamber lenses and iris fixation intraocular lenses. A lid member is provided for securing an intraocular lens within the recessed portions. The lid member can comprise a sliding member in one embodiment or a rotating member in another embodiment. Finally, a sealing member can be provided on one side of the transparent outer housing, for example, of a paper fiber composition that is permeable to a sterilizing gas such as ethylene oxide.

The features of the present invention which are believed to be novel are set forth with particularity in the appended claims. The present invention, both as to its organization and manner of operation, together with further objects and advantages thereof, may best be understood by reference to the following description taken in conjunction with the accompanying drawings.

BRIEF DESCRIPTION OF THE DRAWINGS

FIG. 1 is a side view of a first embodiment of the present invention;

FIG. 2 is a cross-sectional view taken along the line 2—2 of FIG. 1;

FIG. 3 is a perspective view of a support member, intraocular lens and lid member;

FIG. 4 is a plan view of a second embodiment of a support member of the present invention;

FIG. 5 is a cross-sectional view taken along the line 5—5 of FIG. 4, and

FIG. 6 is a cross-sectional view taken along the line 6—6 of FIG. 5.

DESCRIPTION OF THE PREFERRED EMBODIMENTS

The following description is provided to enable any person skilled in the optical and medical implant field to make and use the invention and sets forth the best modes contemplated by the inventor of carrying out his invention. Various modifications, however, will remain readily apparent to those skilled in the art since the generic principles of the present invention have been defined herein specifically to provide a relatively economically and easily manufactured embodiment through injection plastic molding.

An intraocular artificial lens comprises broadly an optical lens component and appropriate peripheral haptic retention member. These retention members can be of a solid configuration integrally molded with the optical lens portion or can be loops and staves that are subsequently attached to the lens member, for example, of PROLENE material. The lenses can be positioned in the anterior chamber of the eye across the iris; affixed to the iris through loops and sutures, or positioned in the posterior chamber of the eye adjacent the ciliary body. In each type of lens, it is important to maintain a consistent optical surface without power variations and to match the diopter power of the lens with that of the recipient patient's subjective needs.

Additionally, a relatively lengthy and expensive procedure is required relating to the sterilization of the lens. The manufacturer has to provide extensive quality control of the sterilization, for example, with ethylene oxide gas and frequently has to run specimen checks with independent labs for each batch of lenses sterilized. If the implanting doctor is forced to break the seal on an intraocular lens, which subsequently cannot be implanted in the patient, but is otherwise acceptable, it is necessary for the manufacturer to then reprocess and resterilize this lens within certain accepted standards of the quantity of residual ethylene oxide on the individual lens.

Two embodiments of the present invention are disclosed herein in configurations that are particularly adapted to a plastic injection mold process. Referring to FIG. 1, an intraocular lens storage container assembly 2 of the first embodiment of the present invention is disclosed in a side view. As can be seen, with further reference to FIG. 2, a transparent outer housing 4 has a pair of flat parallel walls 6 and 8 that are closed by three side walls to form a rectangular configuration. A lower peripheral flange 10 provides structure for sealing the transparent outer housing 4 to maintain a sterile environment for the intraocular lens. A pair of internal guide rims 12 and 14 are dimensioned to retain a support member 16 configured to fit within the transparent outer housing 4.

Referring to FIG. 3, a perspective view of the support member 16 is disclosed and includes a base plate 18 having a downwardly extending peripheral rim 20 and an elevated shoulder portion 22 about an aperture 24 extending through the support member 16. A plurality of recessed portions or cavities 26 are spaced in the support member 16 about the aperture 24. The configuration, dimension and also radial position of these recessed cavities are particularly adapted to accommodate the haptic configuration of one or more different styles of intraocular lens. Thus, the container assembly 2 has universal application for most types of intraocular lenses.

Mounting apertures 28 and 30 are positioned radially outward from the shoulder portion 22 and have a variable inner radial surface to permit a locking rotational interfacing with retaining tines 32 and 34 positioned on a removable lid member 36. The lid member 36 also contains an aperture 38 that can be concentrically aligned with the aperture 24 on the support member 16 when the lid member 36 is secured thereto. The bottom surface of the lid member 36 contacts the upper surface of the shoulder portion 22 of the support member 16 to cover the corresponding side cavities adjacent the aperture 24 for receiving the haptic portions of the intraocular lens 40.

As shown in FIG. 3, an anterior chamber intraocular lens 40 is disclosed with solid haptic foot pads, however, it should be realized that loops, staves, half loops and other forms of haptic retaining members could likewise fit within the haptic retention recesses about the aperture 24.

As an additional feature, the diametrical dimension of the recesses can vary and can be so identified as shown in FIG. 3 to identify a specific length for the lens that would accommodate the particular measurement of a patient's eye. As can be appreciated by a person skilled in this field, both the diopter power and size of the lens are subjectively determined for a particular patient. Both of these features are checked by the implanting doctor prior to the installation of the lens in the patient's eye.

Accordingly, an intraocular lens such as 40 is appropriately mounted within the recesses 26 according to its length. The optic portion or zone which in this case is a plano convex lens is mounted across the aperture 24. The retaining lid member 36 is then positioned so that the locking tines 32 and 34 enter the entrance portion of the apertures 30 and 28 thereby permitting the bottom surface of the lid member 36 to come into contact with the upper surface of the shoulder portion 22. The lid member 36 is then relatively rotated clockwise to the support member 16 to lock the intraocular lens 40 into a final storage position. The support member 16 is then slid into the outer housing 4 along the guide rims 12 until it comes into contact with the upper inside surface of the housing 4. The height of the lid member 36 is of such a dimension to permit a snug fit with the interior surface of the flat wall 8.

Filter paper 42 is then appropriately sealed on the mounting peripheral flanges 10. The filter paper 42 has capillaries of such a dimension to permit the penetration of a sterilizing gas such as ethylene oxide while preventing the penetration of microbes such as viruses that could affect the sterility of the intraocular lens 40. The storage container assembly 2 with the intraocular lens 40 can then be treated with other similar lens assemblies in a container for sterilization with ethylene oxide gas.

Since the housing 4 has flat transparent walls 6 and 8, that are capable of transmitting light without any substantial distortion, the implanting doctor can visually observe the condition of the intraocular lens and in particular the optical zone as it is suspended within the aperture openings of the lid member 36 and support member 16. This can be accomplished without the necessity of breaching the seal 42. Thus, the implanting doctor is capable of performing a preliminary verification of the optical quality and even size of the intraocular lens prior to opening the container assembly 2.

Referring to FIGS. 4, 5 and 6, an alternative embodiment of a support member 44 is disclosed having an appropriate configuration and dimension for securement within the container assembly 2. The support member 44 includes a base plate 46 having a pair of apertures 48 and 50 extending throughout the base plate 46. A stop member 52 rises from the surface of the base plate 46 and defines a limitation of travel of a sliding lid member 54. An elevated shoulder portion 56 extends upward from the support surface 46 and is capable of providing a slight frictional fit with a closed end of the lid member 54. A second shoulder portion 58 has a peripheral dove tail configuration and is designed to coact on its peripheral edges with retaining flanges 60 and 62 that extend along the length of the lid member 54.

Surrounding and extending radially outward from the aperture 48 is a recessed cavity portion 64, that is recessed relative to the second shoulder portion 58, designed to retain the haptic portion of an intraocular lens. Likewise, concentrically surrounding the aperture 50 is a recessed cavity portion 66 having a plurality of post members 68 extending upward from the recessed surface to approximately the elevation of the second shoulder portion 58. The post members 68 are capable of receiving the haptic loops of certain styles of intraocular lenses and retaining the same so that the optic portion or zone of the intraocular lens is positioned across the aperture 50.

The sliding lid member 54 includes a pair of apertures 70 and 72 that are longitudinally positioned on the lid member to be aligned with the respective apertures 48 and 50 when the sliding lid member 54 has been positioned against the stop member 52. A beveled recess surface is provided about each of the apertures 70 and 72, while a raised handle rail 74 is provided simply to assist the relative movement of the sliding lid member 54 across the support member 44.

By providing the pair of apertures with different configurations of the recessed cavity portions 64 and 66, it is possible to accommodate different styles of intraocular lenses for mounting within the container assembly 2 on the same support member 44. As a practical matter, only one intraocular lens will be generally stored on a support member.

As can be appreciated, the first embodiment disclosed in FIGS. 1, 2 and 3 could assume the configuration of FIG. 4 in providing posts for securement of intraocular lenses with haptic loops. As should be appreciated, the relative size of the storage assembly has been enlarged for purposes of illustration and the drawings are not drawn to actual size. It should also be appreciated that the provision of apertures on both the support member and the complimentary lid member is to facilitate the least distortion of light and to provide unobstructed access to the ethylene oxide gas during the sterilization process. The provision of a solid transmitting area capable of transmitting light without any substantial distortion across the optic zone of the intraocular lens could achieve the same purpose of permitting inspection without breaching the sterile environment of the intraocular lens. Thus, a thin planar section of transparent plastic could be placed across the present aperture without substantially affecting the desired results of the present invention, as long as there is no distortion of the transmitting light that would affect a determination of the diopter power of the optic portion of the intraocular lens.

Since the principles of the present invention have been disclosed in the preferred embodiments for mass commercial production, it should be appreciated that other variations of the invention could be accomplished within the generic principles set forth herein, and accordingly, the scope of the present invention should be determined solely from the following claims wherein I claim:

What is claimed is:

1. An intraocular lens storage container assembly for permitting the visual inspection of the lens portion of the intraocular lens without removal from the container, comprising:
    a transparent outer housing having a pair of walls capable of transmitting light without any substantial distortion;
    a support member configured to fit within the transparent outer housing having at least one transmitting area permitting the transmission of light without any substantial distortion and a recess portion of such a dimension and configuration adjacent the transmitting area to receive the haptic portions of an intraocular lens while positioning the lens portion over the area, and
    means for securing an intraocular lens within the recess portion.

2. The invention of claim 1 wherein the means for securing an intraocular lens includes a removable lid member having at least one aperture aligned with the transmitting area on the support member.

3. The invention of claim 2 wherein the removable lid member includes a pair of retaining members and the support member includes a pair of retaining rails that permit a sliding engagement with the retaining members.

4. The invention of claim 2 wherein the removable lid member includes a pair of retaining tines and the support member includes a pair of complimentary apertures having an inner variable radial surface to permit a rotational interfacing with the retaining tines for locking engagement with the support member.

* * * * *